(12) United States Patent
Fukuda (10) Patent No.: US 10,755,449 B2
(45) Date of Patent: Aug. 25, 2020

(54) TOMOGRAPHIC IMAGE PROCESSING DEVICE, TOMOGRAPHIC IMAGE PROCESSING METHOD, AND TOMOGRAPHIC IMAGE PROCESSING PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 15/884,384

(22) Filed: Jan. 31, 2018

(65) Prior Publication Data

US 2018/0268573 A1  Sep. 20, 2018

(30) Foreign Application Priority Data

Mar. 17, 2017 (JP) ................................. 2017-052329

(51) Int. Cl.
*A61B 6/00* (2006.01)
*A61B 6/03* (2006.01)
(Continued)

(52) U.S. Cl.
CPC .......... *G06T 11/003* (2013.01); *A61B 6/5235* (2013.01); *A61B 6/5282* (2013.01);
(Continued)

(58) Field of Classification Search
None
See application file for complete search history.

(56) References Cited

U.S. PATENT DOCUMENTS 7,065,234 B2 * 6/2006 Du .................... A61B 6/5282
382/131
7,463,712 B2 * 12/2008 Zhu .................... A61B 6/5282
378/2
(Continued)

FOREIGN PATENT DOCUMENTS

CN 104408753 3/2015
JP 2007300964 11/2007
(Continued)

OTHER PUBLICATIONS

Dinko E. Gonzalez Trotter, et al., "Thickness-dependent scatter correction algorithm for digital mammography," Proc. SPIE 4682, Medical Imaging 2002: Physics of Medical Imaging, (May 3, 2002); doi: 10.1117/12.465591 (Year: 2002).*
(Continued)

*Primary Examiner* — Soo Shin
(74) *Attorney, Agent, or Firm* — JCIPRNET (57) ABSTRACT

An image acquisition unit acquires a plurality of projected images from a CT apparatus. A reconstruction unit reconstructs the plurality of projected images to produce a plurality of tomographic images. A scattered ray removal unit removes scattered ray components included in radiation transmitted through the subject from the plurality of projected images based on the tomographic images. The repetition unit performs repetition processing of repeating production of a new tomographic image obtained by reconstructing the projected images from which the scattered ray components are removed, and the removal of the scattered ray components from the plurality of projected images based on the new tomographic image.

8 Claims, 4 Drawing Sheets

(51) Int. Cl.
*G01B 15/02* (2006.01)
*G01N 23/046* (2018.01)
*G06T 11/00* (2006.01)
*G06T 5/00* (2006.01)
*G06T 7/00* (2017.01)

(52) U.S. Cl.
CPC ............ *G01B 15/02* (2013.01); *G01N 23/046* (2013.01); *G06T 5/003* (2013.01); *G06T 7/0012* (2013.01); *G06T 11/005* (2013.01); *A61B 6/032* (2013.01); *A61B 6/4476* (2013.01); *A61B 6/5205* (2013.01); *A61B 2576/00* (2013.01); *G01N 2223/401* (2013.01); *G06T 2207/10081* (2013.01)

(56) References Cited

U.S. PATENT DOCUMENTS

| | | | |
|---|---|---|---|
| 8,064,676 B2* | 11/2011 | Li | A61B 6/00 382/132 |
| 8,620,053 B2* | 12/2013 | Michel | G06T 11/005 382/131 |
| 9,704,241 B2 | 7/2017 | Imai | |
| 9,824,467 B2* | 11/2017 | Litvin | G06T 11/005 |
| 9,842,395 B2 | 12/2017 | Imai | |
| 2006/0008046 A1* | 1/2006 | Ruhrnschopf | A61B 6/032 378/7 |
| 2007/0242794 A1* | 10/2007 | Stanton | A61B 6/02 378/5 |
| 2007/0268996 A1 | 11/2007 | Hagiwara et al. | |
| 2010/0284596 A1* | 11/2010 | Miao | G06T 11/005 382/131 |
| 2011/0274252 A1* | 11/2011 | Kuwabara | A61B 6/4291 378/155 |
| 2013/0028496 A1* | 1/2013 | Panin | G06T 11/006 382/131 |
| 2013/0051516 A1* | 2/2013 | Yang | A61B 6/03 378/4 |
| 2013/0051519 A1* | 2/2013 | Yang | G06T 11/005 378/19 |
| 2013/0129178 A1* | 5/2013 | Wieczorek | G06T 11/006 382/131 |
| 2015/0379711 A1* | 12/2015 | Imai | G06T 7/0012 382/132 |
| 2016/0140720 A1* | 5/2016 | Naito | A61B 6/4291 382/132 |
| 2018/0235562 A1* | 8/2018 | Petschke | A61B 6/5205 |
| 2018/0325485 A1* | 11/2018 | Maslowski | G06T 7/0012 |

FOREIGN PATENT DOCUMENTS

| | | |
|---|---|---|
| JP | 2014207958 | 11/2014 |
| JP | 2015043959 | 3/2015 |
| WO | 2006070316 | 7/2006 |

OTHER PUBLICATIONS

Dinko E. Gonzalez Trotter, et al., "Thickness-dependent scatter correction algorithm for digital mammography," Proc. SPIE 4682, Medical imaging 2002: Physics of Medical Imaging, May 3, 2002 (Year: 2002).*

Office Action of Japan Counterpart Application, with English translation thereof, dated Jan. 7, 2020, pp. 1-6.

* cited by examiner

TOMOGRAPHIC IMAGE PROCESSING DEVICE, TOMOGRAPHIC IMAGE PROCESSING METHOD, AND TOMOGRAPHIC IMAGE PROCESSING PROGRAM

CROSS REFERENCE TO RELATED APPLICATIONS

The present application claims priority under 35 U.S.C. § 119 to Japanese Patent Application No. 2017-052329 filed on Mar. 17, 2017. The above application is hereby expressly incorporated by reference, in its entirety, into the present application.

BACKGROUND

Field of the Invention

The present invention relates to a tomographic image processing device, a tomographic image processing method, and a tomographic image processing program that performs the processing of removing scattered ray components included in tomographic images acquired by a computed tomography (CT) apparatus or the like.

Description of the Related Art

In the related art, in a case where the thickness of a subject is large in a case where a radiation image of the subject is captured with radiation transmitted through the subject, there is a problem that the radiation is scattered within the subject to produce scattered rays and the contrast of the acquired radiation image decreases by these scattered rays. For this reason, in a case where the radiation image is captured, the capturing may be performed by disposing a scattered-ray removal grid (hereinafter simply referred to as a grid) between the subject and a radiation detector for detecting the radiation to acquire the radiation image such that the radiation detector is not irradiated with the scattered rays. Since the radiation detector is not easily irradiated with the radiation scattered by the subject in a case where capturing is performed using the grid, the contrast of the radiation image can be improved.

Since the grid is configured such that lead through which radiation is not transmitted, and an interspace material through which radiation is apt to be transmitted, such as aluminum or fiber, are alternately disposed, for example, in a fine lattice density of about 4.0 pieces/mm, the grid is heavy. For this reason, it is necessary to dispose the grid between a patient who is lying down and the radiation detector, in portable imaging to be performed in a hospital ward or the like. As a result, a burden on the work of arrangement and a burden on the patient during the imaging become large. Additionally, in the case of a convergence type grid, there is a concern that density unevenness may occur in the radiation image due to oblique incidence of the radiation. Additionally, there is a concern that a finely striped pattern (moire) corresponding to the pitch of the grid may be recorded on the radiation image together with a subject image and the radiation image may become difficult to see.

For this reason, a radiation image is captured without using the grid, and giving an image-quality improving effect resulting from the removal of scattered rays by the grid to the radiation image through image processing is performed (refer to JP2014-207958A). In the technique of JP2014-207958A, the characteristics of the grid assumed to be used in order to remove scattered rays during the capturing of the radiation image are acquired, a scattered ray component included in the radiation image is estimated on the basis of the characteristics, and scattered ray removal processing is performed using the estimated scattered ray component. Additionally, in a case where a tomographic image is acquired from a projected image acquired by a CT apparatus or the like, a technique of calculating the density distribution of an imaging region of a subject on the basis of a tomographic image, estimating a scattered ray component on the basis of the density distribution, removing the estimated scattered ray component from the projected image, and producing a tomographic image from the projected image from which the scattered ray component is removed is suggested (refer to JP2007-300964A). Moreover, a technique of estimating the body thickness of a subject on the basis of a tomographic image, estimating a scattered ray component using the estimated body thickness, and performing scattered ray removal processing of a radiation image is also suggested (refer to JP2015-43959A).

SUMMARY

However, in the technique described in the above-described JP2007-300964A, it is difficult to make the scattered ray component estimated on the basis of the tomographic image completely coincide with the scattered ray component included in the projected image. For this reason, even in a case where the scattered ray component estimated on the basis of the tomographic image is removed from the projected image, there is a concern that the scattered ray component may remain. In this way, in a case where the scattered ray component cannot be accurately removed from the projected image, the quality of the tomographic image produced again from the projected image from which the scattered ray component is removed cannot be improved.

The invention has been made in view of the above circumstances, and an object thereof is to accurately remove scattered ray components included in tomographic images.

A tomographic image processing device according to the invention comprises reconstruction unit for moving a radiation source relative to detection unit, and reconstructing a plurality of projected images that are captured by irradiating the subject with radiation at a plurality of radiation source positions according to the movement of the radiation source and respectively correspond to the plurality of radiation source positions, thereby producing a tomographic image of the subject; and scattered ray removal unit for removing scattered ray components included in radiation transmitted through the subject from the plurality of projected images, on the basis of the tomographic image. The reconstruction unit produces reconstructed projected images from which the scattered ray components are removed, thereby producing a new tomographic image. The tomographic image processing device further comprises repetition unit for controlling the reconstruction unit and the scattered ray removal unit so as to perform repetition processing of repeating the removal of the scattered ray components from the plurality of projected images based on the new tomographic image and production of a newer tomographic image obtained by reconstructing the plurality of projected images from which the scattered ray components are removed on the basis of the new tomographic image.

In addition, in the tomographic image processing device according to the invention, the scattered ray removal unit may calculate a body thickness of the subject for each of the plurality of projected images from the tomographic image.

Additionally, in the tomographic image processing device according to the invention, the scattered ray removal unit may calculate the body thickness for each of the plurality of projected images on the basis of a region of the subject in the tomographic image.

In addition, in the tomographic image processing device according to the invention, the scattered ray removal unit may estimate each scattered ray component on the basis of the body thickness for each of the plurality of projected images.

Additionally, in the tomographic image processing device according to the invention, the repetition unit may end the repetition processing in a case where a variation between the new tomographic image and the tomographic image produced before the new tomographic image is produced becomes less than a threshold value.

Additionally, in the tomographic image processing device according to the invention, the repetition unit may end the repetition processing after the repetition processing is performed by a predetermined number of times.

In this case, in the tomographic image processing device according to the invention, the repetition unit may increase the predetermined number of times as the body thickness of the subject is larger.

Additionally, in the tomographic image processing device according to the invention, the reconstruction unit may produce the tomographic image by a successive approximation reconstruction method.

The successive approximation reconstruction method is a technique of repeating, reconstructing a projected image to produce a tomographic image, producing a projected image from the tomographic image through simulation of a process in which a subject is projected on detection unit during imaging, calculating a difference between the produced projected image and the projected image detected by the detection unit, and estimating and reconstructing a tomographic image such that the difference becomes small.

Additionally, in the tomographic image processing device according to the invention, the scattered ray removal unit may perform the scattered ray removal processing on the basis of virtual grid characteristics that are characteristics of a virtual grid assumed to be used in order to remove a scattered ray in a case where the projected image is captured.

A tomographic image processing method according to the invention comprises moving a radiation source relative to detection unit, and reconstructing a plurality of projected images that are captured by irradiating the subject with radiation at a plurality of radiation source positions according to the movement of the radiation source and respectively correspond to the plurality of radiation source positions, thereby producing a tomographic image of the subject; removing scattered ray components included in radiation transmitted through the subject from the plurality of projected images, on the basis of the tomographic image; producing reconstructed projected images from which the scattered ray components are removed, thereby producing a new tomographic image; and performing repetition processing of repeating the removal of the scattered ray components from the plurality of projected images based on the new tomographic image and production of a newer tomographic image obtained by reconstructing the plurality of projected images from which the scattered ray components are removed on the basis of the new tomographic image.

In addition, a program for causing a computer to perform the tomographic image processing method according to the invention may be provided.

Another tomographic image processing device according to the invention comprises a memory that stores commands for causing a computer to perform execution and a processor configured to execute the stored commands. The processor executes reconstruction processing for moving a radiation source relative to detection unit, and reconstructing a plurality of projected images that are captured by irradiating the subject with radiation at a plurality of radiation source positions according to the movement of the radiation source and respectively correspond to the plurality of radiation source positions, thereby producing a tomographic image of the subject; scattered ray removal processing for removing scattered ray components included in radiation transmitted through the subject from the plurality of projected images, on the basis of the tomographic image; and repetition processing for controlling the reconstruction unit and the scattered ray removal unit so as to produce reconstructed projected images from which the scattered ray components are removed, thereby producing a new tomographic image and to perform repetition processing of repeating the removal of the scattered ray components from the plurality of projected images based on the new tomographic image and production of a newer tomographic image obtained by reconstructing the plurality of projected images from which the scattered ray components are removed on the basis of the new tomographic image.

According to the invention, the tomographic image of the subject is acquired by reconstructing the plurality of projected images, and the scattered ray components included in the radiation transmitted through the subject are removed from the plurality of projected images on the basis of the tomographic image. Also, the new tomographic image obtained by reconstructing the projected images from the scattered ray components are removed is produced. Moreover, the tomographic image is produced by performing the repetition processing of repeating the removal of the scattered ray components from the plurality of projected images based on the new tomographic image and production of a newer tomographic image obtained by reconstructing the plurality of projected images from which the scattered ray components are removed, on the basis of the new tomographic image. For this reason, the scattered ray components removed from the projected images on the basis of the tomographic image can be brought close to the scattered ray components included in the projected images by the repetition processing. Hence, the scattered ray components can be accurately removed from the tomographic images, and consequently, a high-definition tomographic image can be obtained.

DESCRIPTION OF THE PREFERRED EMBODIMENTS

Figure 1:
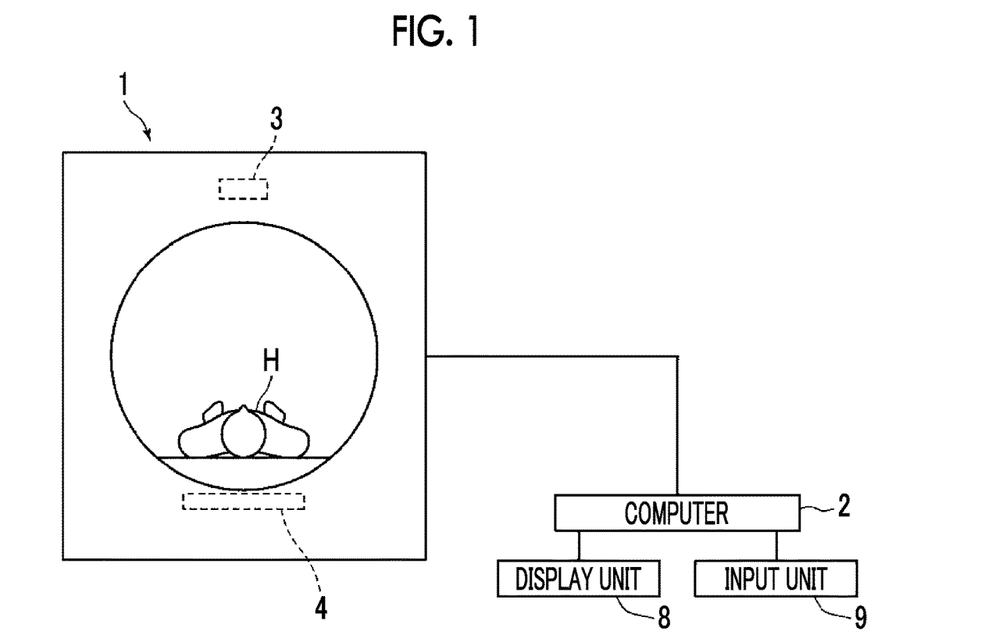
FIG. 1 is a schematic block diagram illustrating the configuration of a tomographic image capturing system to which a tomographic image processing device according to an embodiment of the invention is applied.

Hereinafter, embodiments of the invention will be described with reference to the drawings. FIG. 1 is a schematic block diagram illustrating the configuration of a tomographic image capturing system to which a tomographic image processing device according to an embodiment of the invention is applied. As illustrated in FIG. 1, the tomographic image capturing system according to the present embodiment is for performing various kinds of image processing including scattered ray removal processing on tomographic images produced from a plurality of projected images acquired by a CT apparatus 1, and includes the CT apparatus 1, and a computer 2 including the tomographic image processing device according to the first embodiment is encapsulated, as illustrated in FIG. 1.

The CT apparatus 1 includes a radiation source 3 and a radiation detector 4, moves the radiation source 3 relative to the radiation detector 4, irradiates a subject H with radiation at a plurality of radiation source positions according to the movement of the radiation source 3, thereby imaging the subject H, and acquires a plurality of projected images corresponding to the plurality of radiation source positions, respectively. In addition, in the CT apparatus 1, a grid is not used in a case where the subject H is imaged.

A display unit 8 and an input unit 9 are connected to the computer 2. The display unit 8 is a cathode ray tube (CRT), a liquid crystal display, or the like, and assists in and various kinds of input required for the processing performed in a radiation image acquired by imaging and the computer 2. The input unit 9 is a keyboard, a mouse, or a touch panel.

A tomographic image processing program according to the present embodiment is installed in the computer 2. In the present embodiment, the computer may be a workstation or a personal computer to be directly operated by an operator or may be a server computer connected to the workstation or the personal computer via a network. The tomographic image processing program is recorded on a recording medium, such as a digital versatile disc (DVD) or a compact disc read-only memory (CD-ROM), is distributed, and is installed in the computer from the recording medium. Otherwise, the tomographic image processing program is stored in a storage of the server computer connected to the network, or a network storage stores in a state where an access can be made thereto from the outside, and is downloaded and installed in the computer as required.

Figure 2:
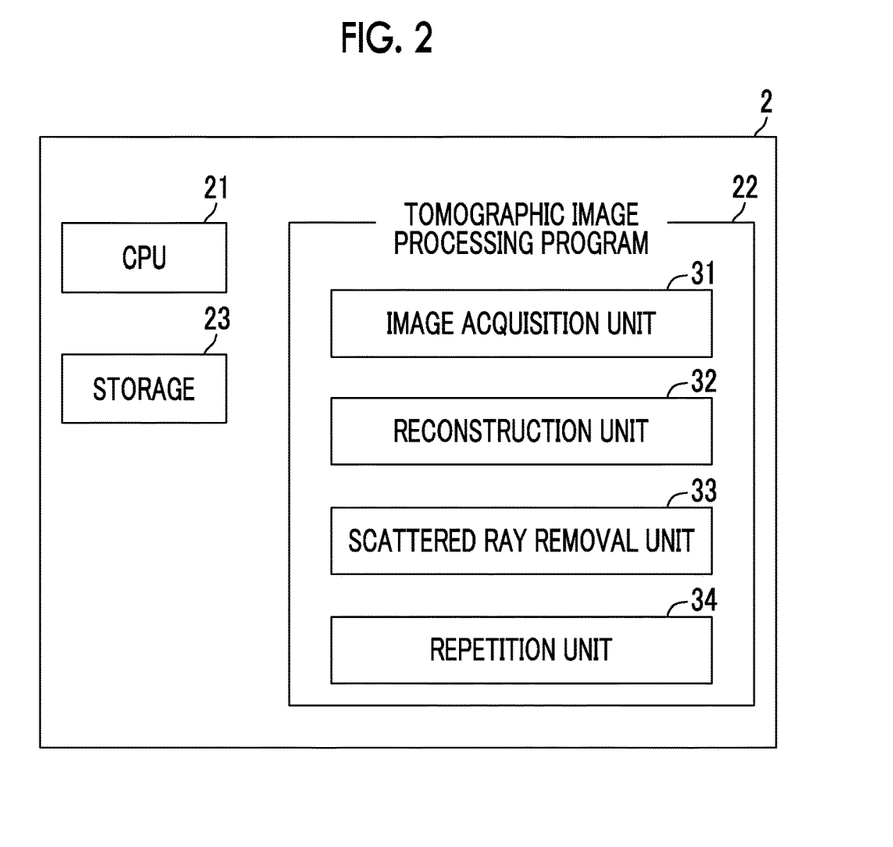
FIG. 2 is a block diagram illustrating a schematic configuration of the tomographic image processing device in the present embodiment.

FIG. 2 is a view illustrating a schematic configuration of the tomographic image processing device realized by installing the tomographic image processing program in the computer 2 in the present embodiment. As illustrated in FIG. 2, the tomographic image processing device includes a central processing unit (CPU) 21, a memory 22, and a storage 23, as components of a standard computer.

The storage 23 is a storage device, such as a hard disk or a solid state drive (SSD), and various kinds of information including programs and stores the tomographic image processing program for driving respective parts of the CT apparatus 1. Additionally, the projected images acquired by the imaging and the tomographic images produced as will be described below are also stored.

In order to cause the CPU 21 to execute various kinds of processing, the programs stored in the storage 23 are temporarily stored in the memory 22. The tomographic image processing program defines, as the processing to be executed by the CPU 21, image acquisition processing for causing the CT apparatus 1 to perform imaging to acquire a plurality of projected images, reconstruction processing for reconstructing the plurality of projected images, thereby producing a tomographic image of the subject H, and reconstructed projected images from which scattered ray components are removed as will be described below, thereby producing a new tomographic image, scattered ray removal processing for removing the scattered ray components included in the radiation transmitted through the subject H, from the plurality of projected images, on the basis of the tomographic images, and repetition processing for performing the repetition processing of repeating the removal of the scattered ray components from the plurality of projected images based on the new tomographic image and production of a newer tomographic image obtained by reconstructing the plurality of projected images from which the scattered ray components are removed on the basis of the new tomographic image.

Then, by executing these kinds of processing in accordance with the tomographic image processing program by the CPU 21, the computer 2 functions as an image acquisition unit 31, a reconstruction unit 32, a scattered ray removal unit 33, and a repetition unit 34. In addition, the computer 2 may include processors or processing circuits that perform the image acquisition processing, the reconstruction processing, the scattered ray removal processing, and the repetition processing, respectively.

The image acquisition unit 31 drives the CT apparatus 1 to move the radiation source 3 and the radiation detector 4 with respect to the subject H, irradiates the subject H with radiation at a plurality of radiation source positions according to the movement of the radiation source 3, and the radiation detector 4 thereby imaging the subject H, and acquires a plurality of projected images Pi (i=2 to n) corresponding to the plurality of radiation source positions, respectively. In addition, a plurality of projected images Pi may be acquired by a program separate from the tomographic image processing program and may be saved in the storage 23. In this case, the image acquisition unit 31 reads the projected images Pi saved in the storage 23 from the storage 23 for tomographic image processing.

The reconstruction unit 32 reconstructs the plurality of projected images Pi by a well-known method, such as a successive approximation reconstruction method, to produce tomographic images Dj (j=1 to m) of the subject H. In addition, as the successive approximation reconstruction method, for example, a technique described in US Patent App. No. 2011/0262054, US Patent No. 2012/0155728, or the like can be used. Additionally, in the present embodiment, the tomographic images Dj are tomographic images in axial sections perpendicular to a body axis of the subject H. Additionally in the present embodiment, it is assumed that the plurality of tomographic images Dj are produced with respect to the plurality of tomographic layers of the subject H.

Figure 3:
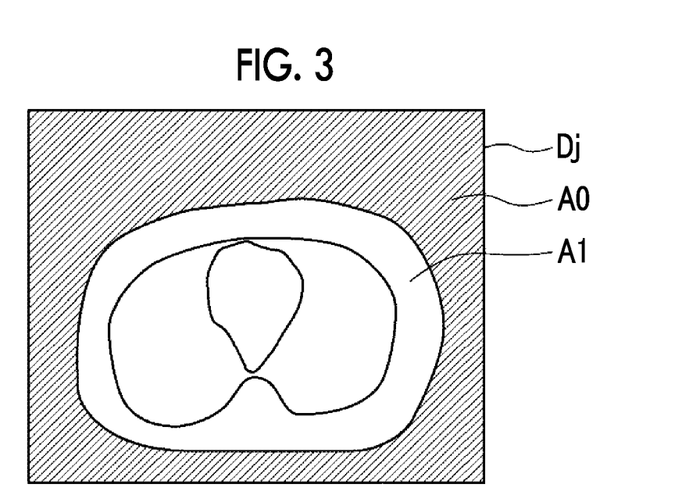
FIG. 3 is a view illustrating a tomographic image.

The scattered ray removal unit 33 removes the scattered ray components included in the radiation transmitted through the subject H, on the basis of the tomographic images Dj. For this reason, the scattered ray removal unit 33 first calculates body thicknesses of the subject H on the basis of the tomographic images Dj. FIG. 3 is a view illustrating a tomographic image in a certain tomographic layer. As illustrated in FIG. 3, a subject region A1 and an air region A0 are included in a tomographic image Dj. Here, CT values are greatly different between the subject region A1 and the air region A0. For this reason, the scattered ray removal unit 33 splits the tomographic image Dj into the subject region A1 and the air region A0 depending on threshold value processing.

Figure 4:
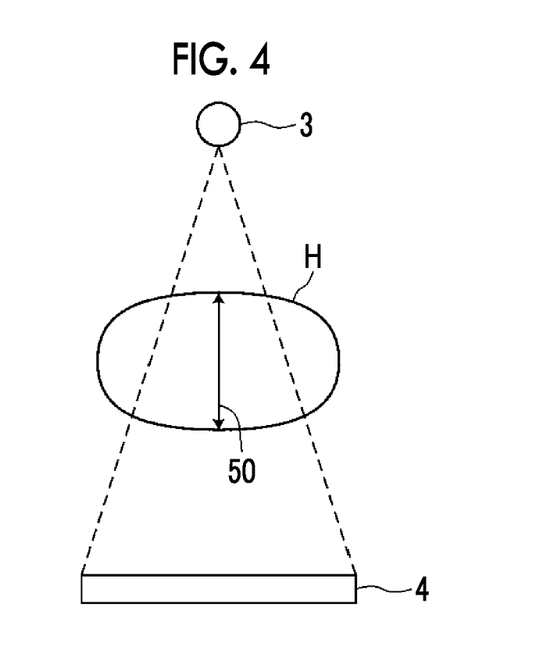
FIG. 4 is a view for describing the calculation of a body thickness in a certain tomographic layer.
Figure 5:
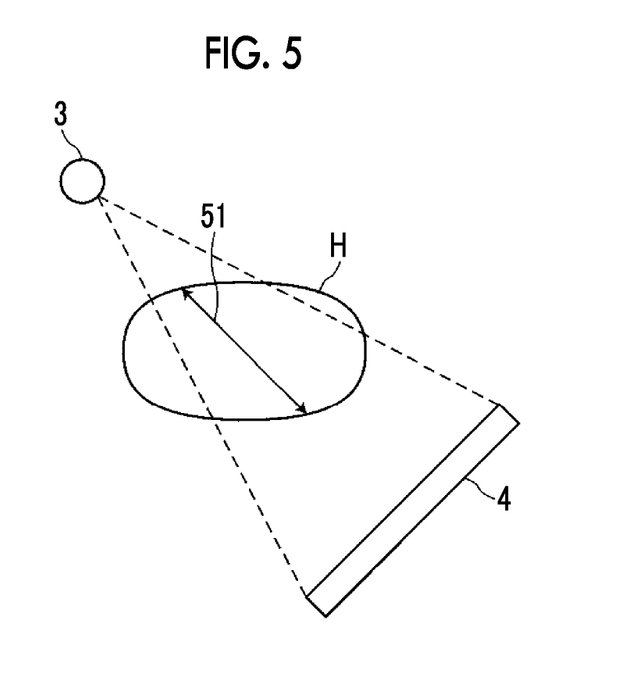
FIG. 5 is a view for describing the calculation of a body thickness in a certain tomographic layer.
Figure 6:
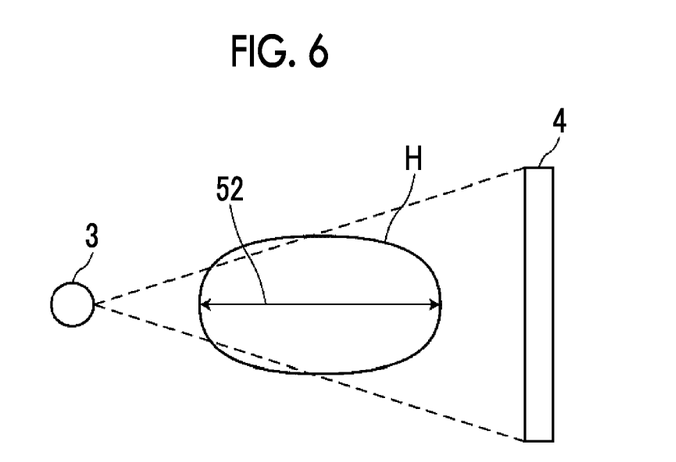
FIG. 6 is a view for describing the calculation of a body thickness in a certain tomographic layer.

Then, the scattered ray removal unit 33 calculates the respective body thicknesses of the subject H for the plurality of projected images Pi from the plurality of the tomographic images Dj. FIGS. 4 to 6 are views for describing the calculation of body thicknesses in certain tomographic layers. In the present embodiment, since the projected images are captured in the CT apparatus 1, as illustrated in FIGS. 4 to 6, the plurality of projected images Pi are acquired at the plurality of radiation source positions. Additionally, since incidence angles are different from each other in the radiation for the subject H at the respective radiation source positions, the lengths of paths along which radiation is transmitted through the subject H are different from each other in the respective projected images Pi acquired at the respective radiation source positions. Hence, the body thicknesses of the subject H included for the respective projected images Pi are different from each other.

Here, the scattered ray removal unit 33 performs splitting into the subject region A1 and the air region A0 in the plurality of tomographic images Dj. For this reason, the scattered ray removal unit 33 calculates the body thicknesses in the subject regions A1 included in the respective projected images Pi, at respective pixel positions of the projected images Pi, in the projected images Pi acquired at the respective radiation source positions by using the respective subject regions A1 of the plurality of tomographic images Dj. Here, a relationship between the position of the subject H in the CT apparatus 1 and the respective radiation source positions are known. For this reason, directions according to the radiation source positions in a case where the projected images are acquired are set in the tomographic images Dj, and the scattered ray removal unit 33 acquires the body thicknesses with respect to the respective projected images Pi. For example, at a radiation source position illustrated in FIG. 4, a body thickness is acquired in a direction indicated by arrow 50, a body thickness is acquired in a direction indicated by arrow 51 at a radiation source position illustrated in FIG. 5, and a body thickness is acquired in a direction indicated by arrow 52 at a radiation source position illustrated in FIG. 6.

Figure 7:
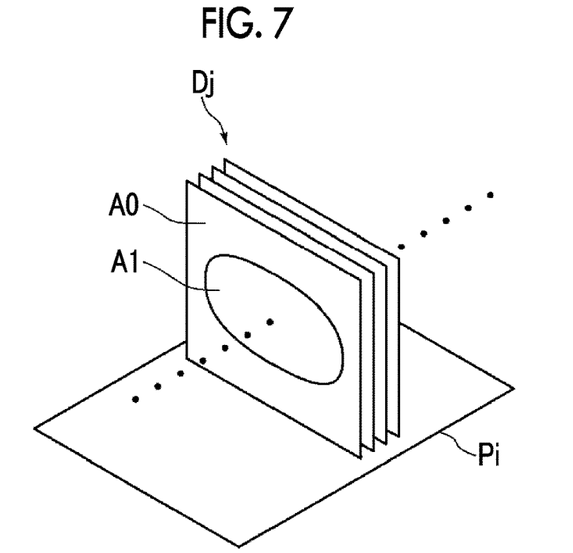
FIG. 7 is a view illustrating a relationship between a plurality of tomographic images and projected images.

Additionally, since the plurality of tomographic images Dj respectively represent the plurality of tomographic layers in the subject H, as illustrated in FIG. 7, the plurality of tomographic images Dj intersect a certain projected image Pi perpendicularly, and a positional relationship between the projected image Pi and the plurality of tomographic images Dj are known. For this reason, body thicknesses at the respective pixel positions in the projected image Pi can be calculated by calculating the body thickness for the plurality of tomographic images Dj. In addition, the intervals of the tomographic images Dj are larger as compared to the intervals of the pixels of the projected image Pi. For this reason, the body thicknesses at the pixel positions of the projected image Pi where the tomographic images Dj are not present may be calculated using the body thicknesses at the pixel positions where the tomographic images Dj are present.

The scattered ray removal unit 33 estimates the scattered ray component of each projected image Pi on the basis of the body thickness for each of the plurality of projected images Pi, and performs the scattered ray removal processing to each projected images Pi. Here, in the present embodiment, no grid is used during imaging. For this reason, the scattered ray removal unit 33 performs the scattered ray removal processing such that the same effect of removing scattered ray as that in a case where imaging is actually performed a grid is given to each projected image Pi. That is, the scattered ray removal unit 33 performs the scattered ray removal processing by using virtual grid characteristics assumed to be actually used. For this reason, the scattered ray removal unit 33 acquires the virtual grid characteristics by the input from the input unit 9 by an operator. In the present embodiment, the virtual grid characteristics are a scattered ray transmittance Ts regarding a virtual grid, and a transmittance (primary ray transmittance) Tp of primary rays transmitted through the subject H and irradiated to the radiation detector 4. In addition, the scattered ray transmittance Ts and the primary ray transmittance Tp have values between 0 and 1.

Also, the scattered ray removal unit 33 calculates a primary ray component Ip and a scattered ray component Is that are included in each projected image Pi, according to the following Expressions (1) and (2), by using the body thickness for each projected image Pi, in order to remove the scattered ray component from each projected image Pi. Moreover, a scattered ray content rate distribution S(x, y) is calculated in Expression (3) from the calculated primary ray component Ip and scattered ray component Is.

$$Ip(x,y)=Io(x,y)\times \exp(-\mu \times T(x,y)) \quad (1)$$

$$Is(x,y)=Io(x,y)*S z\sigma(T(x,y)) \quad (2)$$

$$S(x,y)=Is(x,y)/(Is(x,y)+Ip(x,y)) \quad (3)$$

Here, (x, y) is coordinates of a pixel position of each projected image Pi, Ip(x, y) is a primary ray component at the pixel position (x, y), Is (x, y) is a scattered ray component at the pixel position (x, y), Ioi (x, y) is an incident dos at the pixel position (x, y), T(x, y) is a body thickness at the pixel position (x, y), μ is a ray attenuation coefficient of the subject H, and Sσ (T(x, y)) is a convolution kernel representing the characteristic of scattering according to the body thickness T(x, y) of the subject H at the pixel position (x y). in addition, since the incident dose Io(x, y) to a front surface of the subject H is cancelled in a case where S(x, y) is calculated even in a case where any value is defined, for example, the incident doss Io(x, y) may be set to an arbitrary value, such as being set to 1.

In addition, since the body thickness T(x, y) varies according to the radiation source positions as described above, the body thickness T(x, y) varies for each projected image Pi.

Additionally, the incident dose Io(x, y) varies according to imaging conditions, such as a tube voltage and a mAs value. For this reason, a table in which the various imaging conditions and the incident doses are matched with each other may be stored in the storage 23, and the incident dose Io(x, y) may be obtained with reference to this table from the imaging conditions.

* in Expression (2) is an operator representing convolution calculation. Moreover, Su (T(x, y)) can be experimentally obtained in accordance with the imaging conditions. In the present embodiment, a table in which the various imaging conditions and Sσ (T(x, y)) are matched is stored in the storage 23, and Su (T(x, y)) is obtained with reference to this table from the imaging conditions.

Also, the scattered ray removal unit 33 calculates a conversion factor R(x, y) for converting the projected image Pi according to the following Expression (4) from the scattered ray transmittance Ts and the primary ray transmittance Tp that are the virtual grid characteristics, and the scattered ray content distribution S(x, y). Moreover, the scattered ray removal unit 33 multiplies the conversion factor R(x, y) by the pixel values of the respective pixels of the projected image Pi, according to the following Expression (5), thereby removing a scattered ray component from each projected image Pi, and acquires a processed projected image Psi.

$$R(x,y)=S(x,y)\times Ts+(1-S(x,y))\times Tp \quad (4)$$

$$Psi(x,y)=R(x,y)\times Pi(x,y) \quad (5)$$

In addition, the projected image Pi may be decomposed into a plurality of frequency bands, and the calculation of the conversion factor for each frequency band and the processing of multiplication of the conversion factor may be performed. In this case, a processed projected image Pi is acquired by synthesizing the frequencies of the projected image with the respective frequency bands, which is obtained by multiplying the conversion factor.

Meanwhile, the reconstruction unit 32 produces a new tomographic image Dsj by reconstructing the processed projected images Psi from which the scattered ray components are removed.

The repetition unit 34 controls the reconstruction unit 32 and the scattered ray removal unit 33 so as to perform the repetition processing of repeating the removal of scattered ray components from a plurality of projected images Pi based on the new tomographic image Dsj, similar to the above, and production of a newer tomographic image obtained by reconstructing the plurality of projected images from which the scattered ray components are removed, on the basis of the new tomographic image Dsj.

Here, the repetition unit 34 calculates a variation between the new tomographic image Dsj and the tomographic image Dj in a case where the new tomographic image Dsj is produced. For example, in each tomographic layer where the tomographic image Dsj is calculated, the sum of absolute values of difference values between corresponding pixels of the new tomographic image Dsj and the tomographic image Dj in a corresponding tomographic layer is calculated. In addition, the sum of the squares of the difference values may be calculated instead of the sum of the difference values. Moreover, the further sum of the above sums in all the tomographic layers may be calculated as a variation. In addition, a representative value of difference values between corresponding pixels of the tomographic images Dsj and the tomographic images Dj in all the tomographic layers may be calculated as variations. As the representative value, a minimum value, a maximum value, a mean value, an average value, or the like of the squares or the absolute values of the difference values can be used.

The repetition unit 34 determines whether or not the calculated variation is less than a threshold value Th1. In a case where this determination is negative, the repetition unit 34 repeats the scattered ray removal processing from the projected image Pi based on the new tomographic image Dsj, and the production of a newer tomographic image Dsj obtained by reconstructing the processed projected image Psi acquired by the scattered ray removal processing until above determination is positive. Then, the new tomographic image Dsj produced in a case where the variation is less than the threshold value Th1 is saved as a final tomographic image Dfj in the storage 23.

Figure 8:
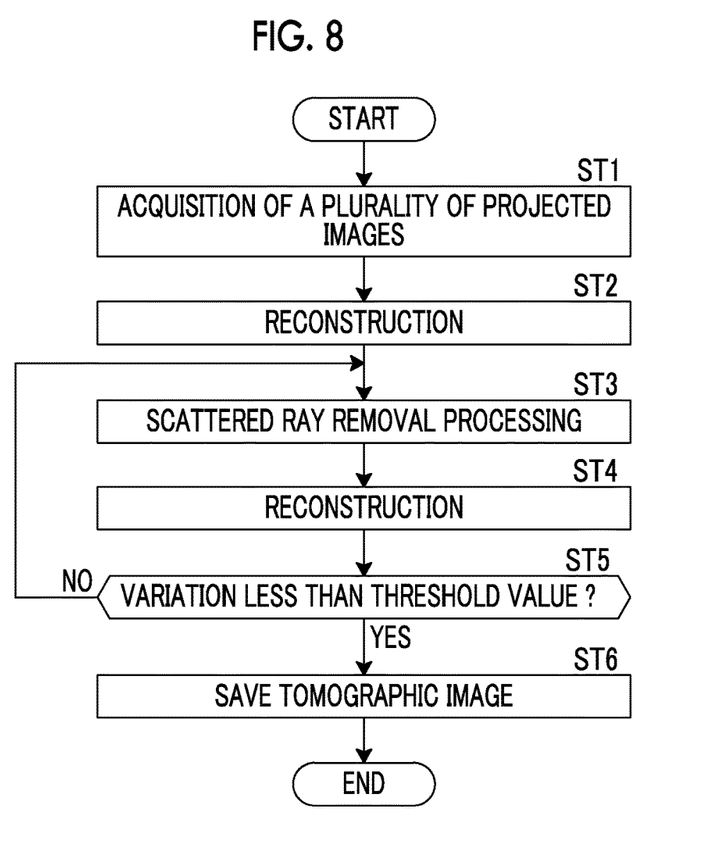
FIG. 8 is a flowchart illustrating the processing performed in the present embodiment.

Next, the processing performed in the present embodiment will be described. FIG. 8 is a flowchart illustrating the processing performed in the present embodiment. First, the image acquisition unit 31 acquires a plurality of projected images Pi from the CT apparatus 1 (Step ST1). Next, the reconstruction unit 32 reconstructs the plurality of projected images Pi, thereby producing a tomographic image Dj of the subject H (Step ST2). Next, the scattered ray removal unit 33 performs the scattered ray removal processing of removing scattered ray components included in the radiation transmitted through the subject H from the plurality of projected images Pi on the basis of the tomographic image Dj, and acquires processed projected images Psi (Step ST3).

Then, the reconstruction unit 32 reconstructs the processed projected images Psi to produce a new tomographic image Dsj (Step ST4). Then, the repetition unit 34 determines whether or not a variation between the new tomographic image Dsj and the tomographic image Dj is less than the threshold value Th1 (Step ST5). In a case where Step ST5 is negative, the process returns to Step ST3 in which the repetition unit 34 repeats the processing of Step ST3 to Step ST5 such that the scattered ray removal unit 33 may perform the scattered ray removal processing from a plurality of projected images based on the new tomographic image Dsj. In a case where Step ST5 is positive, a final tomographic image Dfj is saved as a newest tomographic image Dsj in the storage 23 (Step ST6), and the processing is ended.

In this way, in the present embodiment, and the tomographic image Dfj is produced by reconstructing the plurality of projected images Pi, thereby acquiring the tomographic image Dj of the subject H, removing the scattered ray components from the plurality of projected images Pi on the basis of the tomographic image Dj and reconstructing the projected images Psi from which the scattered ray components are removed, thereby producing the new tomographic image Dsj, and repeating the repetition processing of repeating the removal of the scattered ray components from the plurality of projected images Pi based on the new tomographic image Dsj and the production of the newer tomographic image obtained by reconstructing the plurality of projected images from which the scattered ray components are removed, on the basis of the new tomographic image. For this reason, the scattered ray components removed from the projected images on the basis of the tomographic image can be brought close to the scattered ray components included in the projected images by the repetition processing. Hence, according to the present embodiment, the scattered ray components can be accurately removed from the tomographic images, and consequently, a high-definition tomographic image Dfj can be obtained.

In addition, in the above embodiment, the repetition processing is performed until the variation between the new tomographic image Dsj and the tomographic image Dj becomes less than the threshold value Th1. However, the repetition processing may be predetermined by a predetermined number of times. The number of times of the repetition processing may be set by the input from the input unit 9. Additionally, the scattered ray components included in the projected images increase as the body thickness of the subject H is larger. For this reason, the number of times of the repetition processing as the body thickness of the subject H is larger. In addition, a table in which a relationship between the body thickness of the subject H and the number of times of repetition is saved in the storage 23, and the repetition unit 34 may set the number of times of repetition with reference to this table. As the body thickness of the subject in this case as illustrated in FIG. 4, a maximum value, an average value, or the like of body thicknesses of the respective pixels the projected image by obtained by capturing the subject H from the front.

Additionally, in the above embodiment, whenever the processing of Step ST3 to Step ST4 is repeated, it is determined in Step ST5 whether or not the variation is less than the threshold value Th1. However, whenever the processing of Step ST3 to Step ST4 is repeated by a first predetermined number of times, the processing of Step ST5 may be performed. Additionally, the processing of Step ST3 to Step ST4 may be repeated without performing the processing Step ST5 until a second predetermined number of times after the processing is started, and after the processing being repeated by the second number of times, the processing of Step ST5 may be performed whenever the processing of Step ST3 to Step ST4 is repeated. Additionally, after the processing of Step ST3 to Step ST4 is repeated by the second number of times, the processing of Step ST5 may be performed whenever the processing of Step ST3 to Step ST4 is repeated by the first predetermined number of times.

Additionally, in the above embodiment, the scattered ray removal processing is performed by using the virtual grid characteristics assumed to be actually used. However, the scattered ray removal processing may be performed without using the virtual grid characteristics. In this case, the scattered ray removal processing may be performed by subtracting the scattered ray component $Is(x, y)$ calculated according to the above Expression (2) from each projected image Pi.

Additionally, in the above embodiment, in a case where the tomographic image Dj is produced using the successive approximation reconstruction method in the reconstruction unit 32, this successive approximation reconstruction processing and the above repetition processing may be combined with each other. Here, the successive approximation reconstruction method is performed as follows. First, a projected image is produced by reconstructing a projected image Pi to produce a tomographic image Dj and reversely projecting the tomographic image Dj through simulation of a process in which the subject H is projected on the radiation detector 4. Then, a variation between the produced projected image and an acquired projected image (that is, the projected image Pi acquired by being detected by the radiation detector 4) is calculated. In addition, as the variation, an absolute value of a difference value or the square of the difference value in corresponding pixels of the produced projected image and the acquired projected image can be used. Expression for calculating the absolute value of the difference value as the variation is shown in the following Expression (7). In Expression (7), $Pi(x, y)$ is a pixel value of each pixel of the projected image Pi, and $W \cdot Dj(x, y)$ is a pixel value of each pixel of the projected image produced by projecting the tomographic image Dj. Then, the reconstruction unit 32 repeats reconstruction of a tomographic image using the produced projected image, and production of a new projected image using the newly produced tomographic image until the variation becomes less than a threshold value Th2.

$$\text{Variation} = |Pi(x,y) - W \cdot Dj(x,y)| \qquad (7)$$

Then, the successive approximation reconstruction processing and the above repetition processing are combined together by using a processed projected image Psi subjected to the scattered ray removal processing as $Pi(x, y)$ in Expression (7). In addition, the number of times of repetition of the successive approximation reconstruction method is the number of times until the variation calculated in Expression (7) becomes less than the threshold value Th2, but may be a predetermined number of times. Additionally, the number of times of repetition may be the number of times until the variation between the tomographic image Dj and the new tomographic image Dsj in the repetition processing becomes less than the threshold value Th1. Accordingly, a higher-definition tomographic image in which the influence of a scattered ray is further reduced can be produced.

Additionally, in the above embodiment, the processing in a case where producing the tomographic image from the projected images acquired by the CT apparatus 1 will be described. However, the invention can also be applied to the processing in a case where producing a tomographic image from projected images acquired by tomosynthesis imaging.

Additionally, in the above embodiment, the body thickness of the subject H is calculated by producing the plurality of tomographic images Dj. However, the body thickness of the subject H may be calculated only using one tomographic image Dj. In this case, the body thickness at each pixel position of the projected image Pi may be calculated, for example, by approximating the body thickness of the subject with an elliptical column model from one tomographic image Dj.

Hereinafter, the effects of the present embodiment will be described.

The influence of the scattered ray components becomes larger as the body thickness of the subject is larger. For this reason, the scattered ray components can be more accurately removed from the tomographic images by increasing the number of times of the repetition processing as the body thickness of the subject is larger.

By performing the scattered ray removal processing on the basis of the virtual grid characteristics that are the characteristics of the virtual grid that are assumed in order to remove the scattered ray in a case where the projected images are captured, the tomographic image from which the scattered ray is removed to the same extent as that in a case where a grid assumed to be used is used can be obtained.

What is claimed is:

1. A tomographic image processing device comprising a processor configured to function as a plurality of functional units when instructions are loaded from a memory and executed by the processor, wherein the functional units comprise:

a reconstruction unit for moving a radiation source relative to a detection unit, and reconstructing a plurality of projected images that are captured by irradiating a subject with radiation at a plurality of radiation source positions according to a movement of the radiation source and respectively correspond to the plurality of radiation source positions, thereby producing a plurality of tomographic images of the subject; and a scattered ray removal unit for removing scattered ray components included in radiation transmitted through the subject from the plurality of projected images based on the pluraliy of tomographic images, wherein the reconstruction unit produces reconstructed projected images from which the scattered ray components are removed, thereby producing a pluraliy of new tomographic images, and the functional units further comprise a repetition unit for controlling the reconstruction unit and the scattered ray removal unit so as to perform repetition processing of repeating the removal of the scattered ray components from the plurality of projected images based on the pluraliy of new tomographic images and production of a pluraliy of newer tomographic images obtained by reconstructing the plurality of projected images from which the scattered ray components are removed based on the pluraliy of new tomographic images, wherein the scattered ray removal unit acquires the plurality of projected images at the plurality of radiation source positions for each of the plurality of tomographic images of the subject and calculates a body thickness in a pluraliy of regions of the subject at the plurality of radiation source positions, acquire the body thickness for each of the plurality of tomographic images at respective pixel positions of the tomographic images for the plurality of regions of the subject, calculate body thickness at other pixel positions of the projected images where the plurality of tomographic images of the subject are not present when intervals between the respective pixel positions of the tomographic images are larger than intervals of pixel positions of the projected images, and estimates and removes the scattered ray components of each of the projected images based on the body thickness for each of the plurality of projected images.

2. The tomographic image processing device according to claim 1, wherein the repetition unit ends the repetition processing in a case where a variation between the plurality of new tomographic images and the plurality of tomographic images produced becomes less than a threshold value.

3. The tomographic image processing device according to claim 1, wherein the repetition unit ends the repetition processing after the repetition processing is performed a predetermined number of times.

4. The tomographic image processing device according to claim 3, wherein the repetition unit increases the predetermined number of times as the body thickness of the subject is increases.

5. The tomographic image processing device according to claim 1, wherein the reconstruction unit produces the plurality of tomographic images by a successive approximation reconstruction method.

6. The tomographic image processing device according to claim wherein the scattered ray removal unit performs the scattered ray removal processing based on virtual grid characteristics that are characteristics of a virtual grid in order to remove scattered ray components in a case where the plurality of projected images are captured.

7. A tomographic image processing method comprising:

moving a radiation source relative to a detection unit, and reconstructing a plurality of projected images that are captured by irradiating a subject with radiation at a plurality of radiation source positions according to a movement of the radiation source and respectively correspond to the plurality of radiation source positions, thereby producing a plurality of tomographic images of the subject;

removing scattered ray components included in radiation transmitted through the subject from the plurality of projected images based on the plurality of tomographic images;

producing reconstructed projected images from which the scattered ray components are removed, thereby producing a plurality of new tomographic images; and performing repetition processing of repeating the removal of the scattered ray components from the plurality of projected images based on the plurality of new tomographic images and production of a plurality of newer tomographic images obtained by reconstructing the plurality of projected images from which the scattered ray components are removed based on the plurality of new tomographic images, wherein the step of removing scattered ray components included in radiation transmitted through the subject from the plurality of projected images based on the tomographic image comprises: acquiring the plurality of projected images at the plurality of radiation source positions for each of the plurality of tomographic images of the subject and calculating a body thickness in a plurality of regions of the subject at the plurality of radiation source positions, acquire the body thickness for each of the plurality of projected tomographic images at respective pixel positions of the tomographic images for the plurality of regions of the subject, calculate body thickness at other pixel positions of the projected images where the plurality of tomographic images of the subject are not present when intervals between the respective pixel positions of the tomographic images are larger than intervals of pixel positions of the projected images, and estimating and removing the scattered ray components of each of the projected images based on the body thickness for each of the plurality of projected images.

8. A non-transitory computer-readable recording medium having stored therein a tomographic image processing program causing a computer to perforin:

a procedure of moving a radiation source relative to a detection unit, and reconstructing a plurality of projected images that are captured by irradiating a subject with radiation at a plurality of radiation source positions according to a movement of the radiation source and respectively correspond to the plurality of radiation source positions, thereby producing a plurality of tomographic images of the subject;

a procedure of removing scattered ray components included in radiation transmitted through the subject from the plurality of projected images based on the plurality of tomographic images;

a procedure of producing reconstructed projected images from which the scattered ray components are removed, thereby producing a plurality of new tomographic images; and a procedure of performing repetition processing of repeating the removal of the scattered ray components from the plurality of projected images based on the plurality of new tomographic images and production of a plurality of newer tomographic images obtained by reconstructing the plurality of projected images from which the scattered ray components are removed based on the plurality of new tomographic images, wherein the procedure of removing scattered ray components included in radiation transmitted through the subject from the plurality of projected images based on the tomographic image comprises:

a procedure of acquiring the plurality of projected images at the plurality of radiation source positions for each of the plurality of tomographic images of the subject, a procedure of calculating a body thickness in a plurality of regions of the subject at the plurality of radiation source positions, a procedure of acquiring the body thickness for each of the plurality of tomographic images at respective pixel positions of the tomographic images for the plurality of regions of the subject, a procedure of calculating body thickness at other pixel positions of the projected images where the plurality of tomographic images of the subject are not present when intervals between the respective pixel positions of the tomographic images are larger than intervals of pixel positions of the projected images, and a procedure of estimating and removing the scattered ray components of each of the projected images based on the body thickness for each of the plurality of projected images.

\* \* \* \* \*